United States Patent [19]

Ishikawa et al.

[11] Patent Number: 5,822,033
[45] Date of Patent: Oct. 13, 1998

[54] DIAGNOSTIC APPARATUS FOR MEASURING PUPIL SIZE AND/OR IRIS AREA OF AN EYEBALL

[75] Inventors: Norio Ishikawa; Hidehiro Hosaka, both of Tokyo, Japan

[73] Assignee: Nihon Kohden Corporation, Tokyo, Japan

[21] Appl. No.: 731,016

[22] Filed: Oct. 9, 1996

[30] Foreign Application Priority Data

Oct. 9, 1995 [JP] Japan .................................. 7-261366

[51] Int. Cl.$^6$ ........................................................ A61B 3/14
[52] U.S. Cl. ............................................ 351/210; 351/204
[58] Field of Search ................................... 351/204, 205, 351/206, 210, 212, 247

[56] References Cited

U.S. PATENT DOCUMENTS

| | | | |
|---|---|---|---|
| 4,372,655 | 2/1983 | Matsumura et al. | 351/206 |
| 4,815,839 | 3/1989 | Waldorf | 351/210 |
| 4,850,691 | 7/1989 | Gardner et al. | 351/210 X |
| 4,988,183 | 1/1991 | Kasahara et al. | 351/210 |
| 5,187,506 | 2/1993 | Carter | 351/221 |
| 5,196,873 | 3/1993 | Yamanobe et al. | 351/210 |
| 5,555,895 | 9/1996 | Ulmer et al. | 351/210 |

FOREIGN PATENT DOCUMENTS 0743041  11/1996  European Pat. Off. .

OTHER PUBLICATIONS

Scinto, L.F., Daffner, K.R., Dressler, D., Ransil, B.I., Rentz, D., Weintraub, S., Mesulam, M., Potter, H., "A Potential Noninvasive Neurobiological Test for Alzheimer's Disease", Science, vol. 266, pp. 1051–1054, No. 5187, Nov. 11, 1994.

Science, vol. 166, 11 Nov. 1994, "A Potential Noninvasive Neurobiological Test for Alzheimer's Disease".

*Primary Examiner*—Huy Mai
*Attorney, Agent, or Firm*—Sughrue, Mion, Zinn, Macpeak & Seas, PLLC

[57] ABSTRACT

A CCD camera is supported by a guide rail in such a manner that the camera is be reciprocally movable in the direction toward an opening of a left main unit. When a motor is rotated, the rotation is transmitted to a rack via gears, thereby moving the CCD camera.

5 Claims, 12 Drawing Sheets

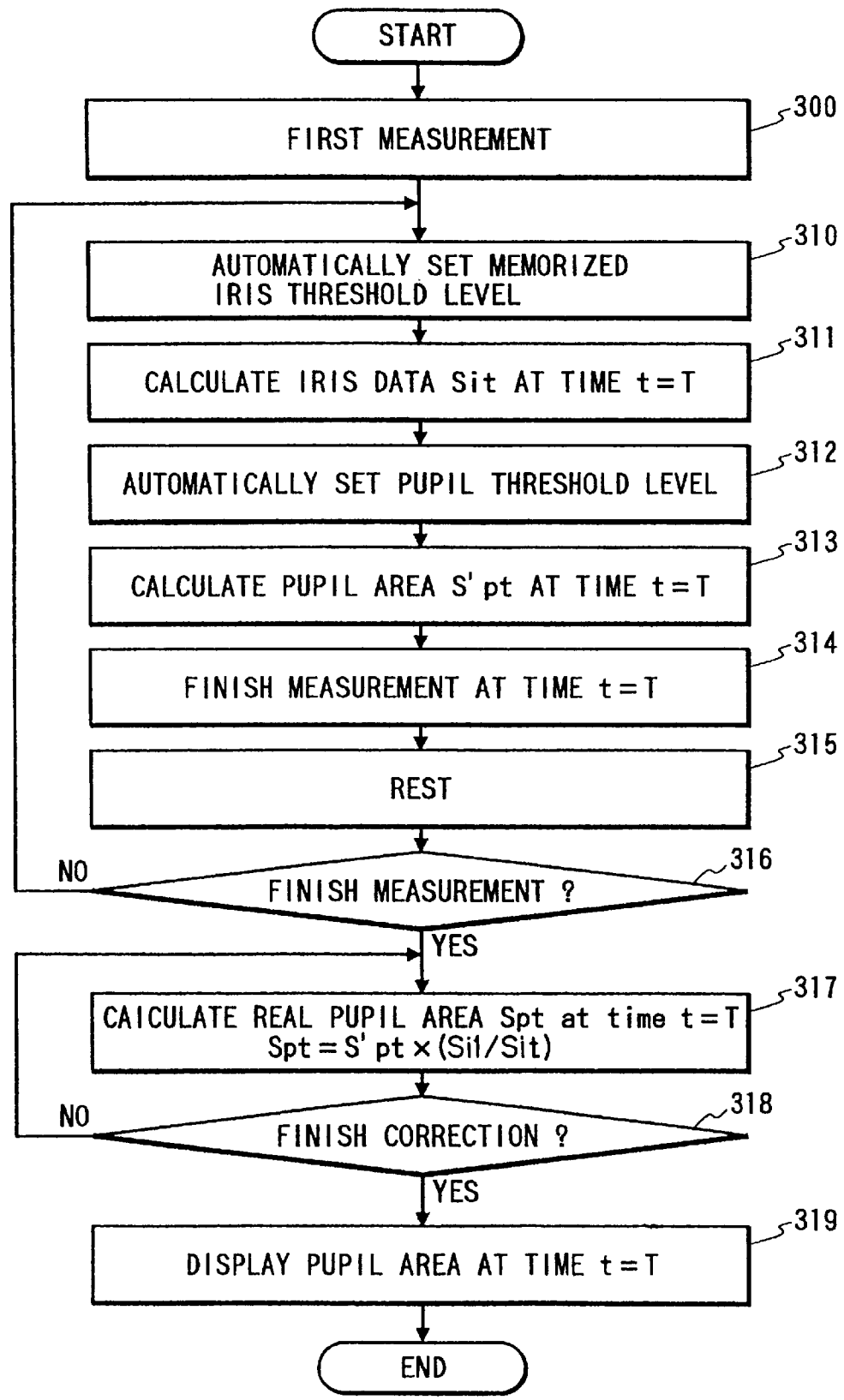

DIAGNOSTIC APPARATUS FOR MEASURING PUPIL SIZE AND/OR IRIS AREA OF AN EYEBALL

BACKGROUND OF THE INVENTION

1. Field of the Invention

The invention relates to an eyeball surface measuring apparatus which conducts measurement on the basis of image data of the eyeball surface obtained from a video camera, such as an apparatus for measuring the pupil, or an apparatus for measuring the motion state of the eyeball, and also to an improvement of a goggle which is used in the measurement.

2. Related Art

Conventional binocular image pick-up equipment used in measuring eye movement and a pupil diameter is provided with video cameras for use with the respective right and left eyes.

Such a construction renders the conventional binocular image pick-up equipment bulky and heavy as a whole, and resultantly expensive. It recently became evident that the measurement of changes in the pupil diameter caused as a result of dropping a pupil-dilating agent into an eye of the patient enables the diagnosis of Alzheimer's disease (SCIENCE, VOL 266, 11 Nov., 1994). It takes a long time to measure the pupil diameter for the diagnosis of Alzheimer's disease. However, as previously mentioned, the conventional binocular image pick-up equipment was bulky and heavy, and hence it was impossible for the patient to wear the equipment for a long period of time.

SUMMARY OF THE INVENTION

The invention has been conducted in view of such defects of the prior art. It is an object of the invention to provide an apparatus in which, when a goggle is mounted on the face, an operation of eliminating an error due to the mounting state of the goggle is not necessary and correct measurement results can be obtained.

According to the present invention, an eyeball surface measuring goggle measures information of an eyeball surface by using an image processing-technique, the goggle comprising: a main unit which is to be mounted on a face of a subject; a video camera; video camera holding means, disposed in the main unit, for, in a state where the main unit is mounted on a face of a subject, holding the video camera in a state where the video camera is directed to an eyeball of the subject, and making the video camera movable in an optical axis of the video camera; and moving means for moving the video camera which is held by the video camera holding means.

The present invention is provided an eyeball surface measuring goggle which measures information of an eyeball surface by using an image processing technique, the goggle comprising: a main unit which is to be mounted on a face of a subject; a video camera; a half mirror disposed in the main unit; video camera holding means, disposed in the main unit, for, in a state where the main unit is mounted on a face of a subject, holding the video camera in a state where the video camera is directed in a direction along which an image of an eyeball of the subject, the image being reflected from the half mirror, and making the video camera movable in an optical axis of the video camera; and moving means for moving the video camera which is held by the video camera holding means.

The present invention is provided an eyeball surface measuring apparatus which comprises an eyeball surface measuring goggle, and which measures an eyeball surface in the goggle, the apparatus further comprising: iris data storing means for storing data indicative of a size which is used as a reference of an iris of an eyeball; and controlling means for supplying a signal to the moving means so that a size of an iris obtained on the basis of the output of the video camera coincides with the size of an iris stored in the iris data storing means, thereby controlling the moving means.

The present invention is provided an eyeball surface measuring apparatus which comprises an eyeball surface measuring goggle comprising: a main unit which is to be mounted on a face of a subject; and a video camera disposed in the main unit, and which measures an eyeball surface on the basis of an output of the video camera disposed in the goggle, the apparatus further comprising: iris data storing means for storing data indicative of a size which is used as a reference of an iris of an eyeball; and correcting means for, in a mounting state in which the main unit is mounted on a face of a subject, correcting a size of a pupil which is obtained on the basis of the output of the video camera, with referencing a size of an iris which is obtained from the output of the video camera in the same mounting state, and the size of the iris which is stored in the iris data storing means.

BRIEF DESCRIPTION OF THE DRAWINGS

FIG. 13 is a flowchart illustrating the operation of the fourth embodiment.

DETAILED DESCRIPTION OF THE PREFERRED EMBODIMENTS

First embodiment

Figure 1:
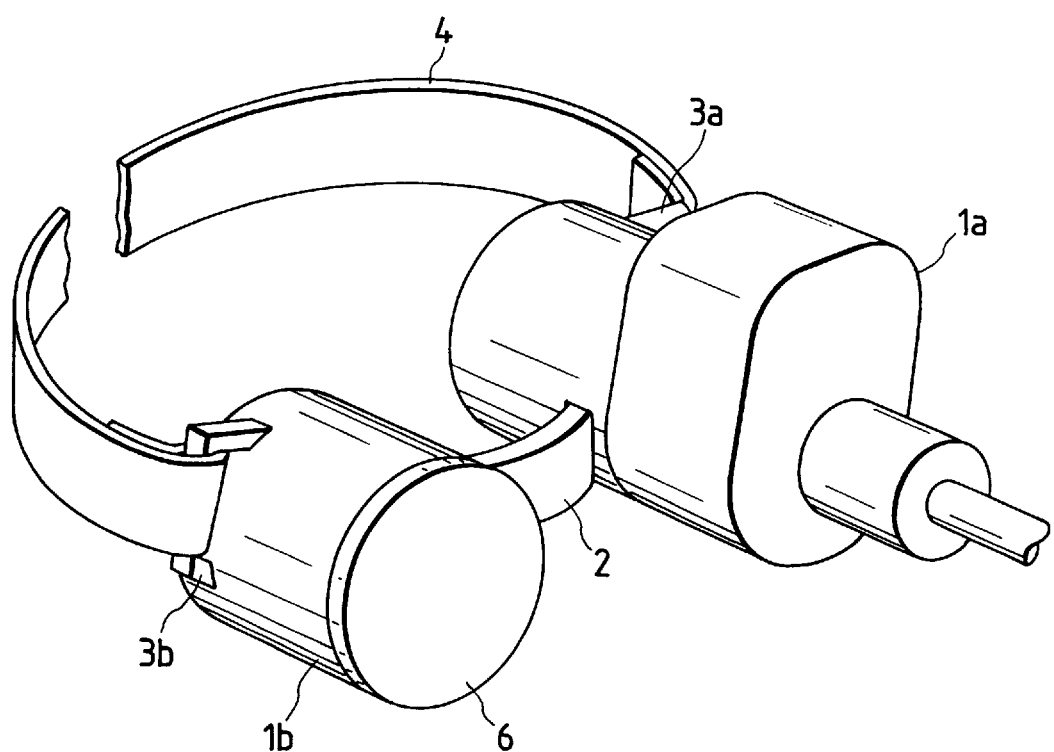
FIG. 1 is a view showing an appearance of a goggle which is used in a first embodiment.
Figure 2:
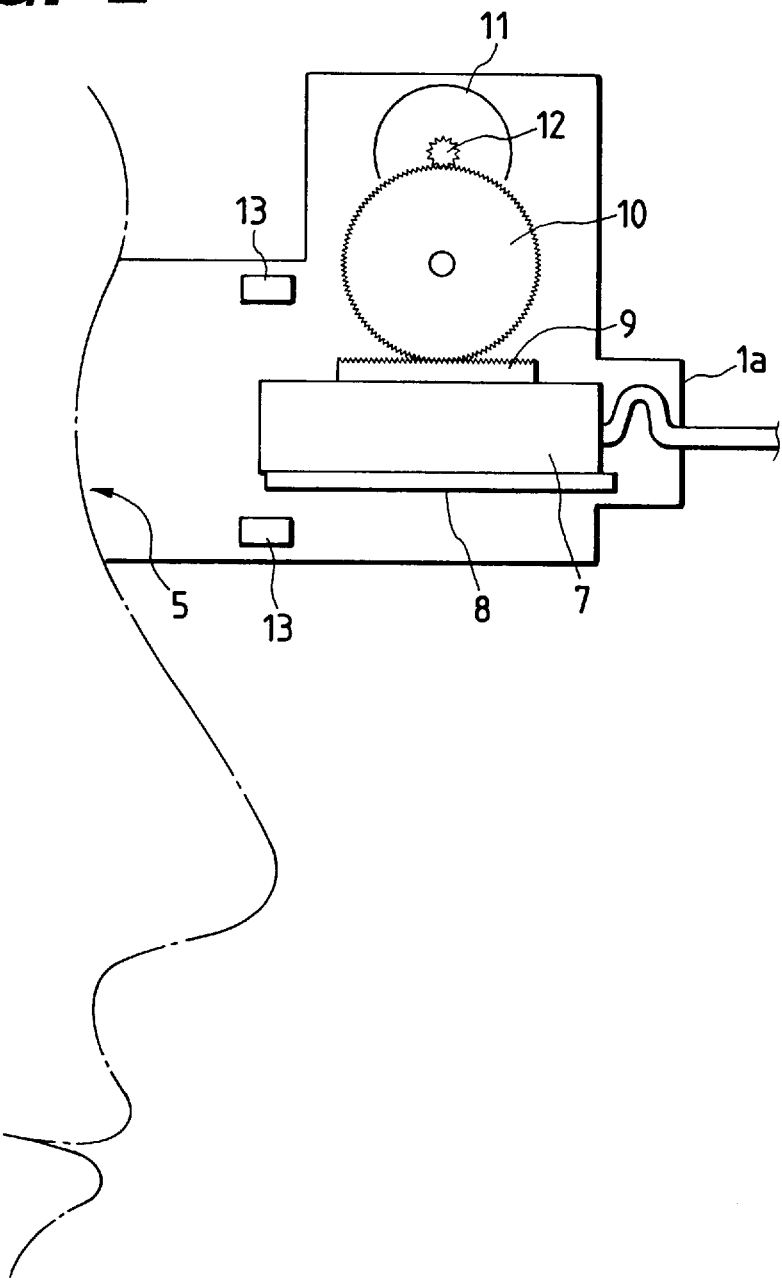
FIG. 2 is a view showing the internal configuration of a left main unit 1a shown in FIG. 1.

A first embodiment of the invention will be described. The eyeball surface measuring apparatus of the embodiment is used as a pupil measuring apparatus. FIG. 1 shows an appearance of a pupil measuring goggle 20 which is used in the first embodiment, and FIG. 2 shows the internal configuration of the goggle. As shown in the figures, a left main unit 1a and a right main unit 1b are connected to each other via a connecting portion 2. Band engaging portions 3a and 3b are projected from the peripheral faces of the main units, respectively. A band 4 is attached to the band engaging portions 3a and 3b. An opening 5 is formed in one end of each of the band engage the edges of the openings 5 have a shape which, when they are pressed against the peripheries of both eyes on the face of a person, is in close contact with the peripheries.

As shown in FIG. 2, a fixed focus CCD camera 7 is disposed in the left main unit 1a so as to be directed toward the opening 5 of the left main unit 1a. By a guide rail 8 attached to the left main unit 1a, the CCD camera 7 is supported and held in such a manner that the camera is reciprocally movable with respect to the opening 5. A rack 9 is attached onto the outer face of the CCD camera 7 so as to elongate in the longitudinal direction of the camera. A gear 10 which meshes with the rack 9 is rotatably attached to the main unit 1a. Furthermore, a motor 11 is attached to the main unit 1a. A gear 12 attached to the rotation shaft of the motor 11 meshes with the gear 10. A plurality of LEDs 13 which emit infrared light are disposed in the left main unit 1a so as to be directed toward the opening 5.

As shown in FIG. 1, the front of the right main unit 1b is closed by a shield plate 6 so that the interior the right main unit forms a cavity. The shield plate 6 is configured so as to be easily attached to and removed from the right main unit 1b. The shield plate is removed from the main unit during the measurement process as described later. In the goggle 20, the CCD camera 7 functions as the video camera, the guide rail 8 as the holding means for holding the video camera, and the means consisting of the motor 11, the gears 10 and 12, and the rack 9 as the moving means for moving the video camera.

Figure 3:
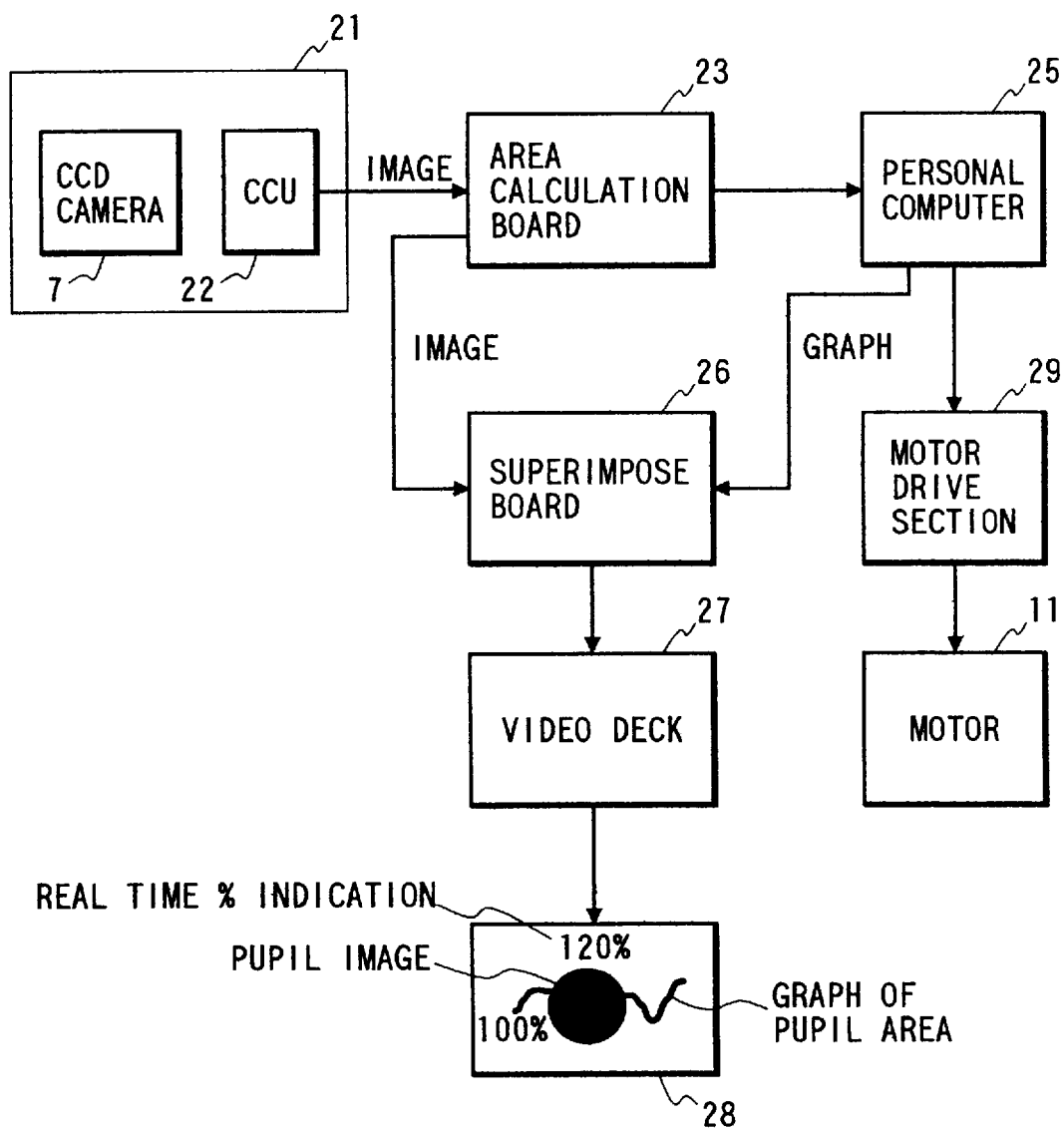
FIG. 3 is a block diagram showing the whole configuration of the first embodiment.

FIG. 3 shows the apparatus for measuring the size of the pupil by using the pupil measuring goggle 20. An imaging apparatus 21 comprises the CCD camera 7 incorporated in the goggle 20, and a CCU (Camera Control Unit) 22 which controls the CCD camera 7.

On the basis of a video signal output from the imaging apparatus 21, an area calculation board 23 calculates the area of a part of an image of one part being not higher than a preset threshold level. A personal computer 25 performs data processing on the basis of digital data of the area which are supplied from the area calculation board 23, and outputs results of the processing and also control signals.

Figure 4:
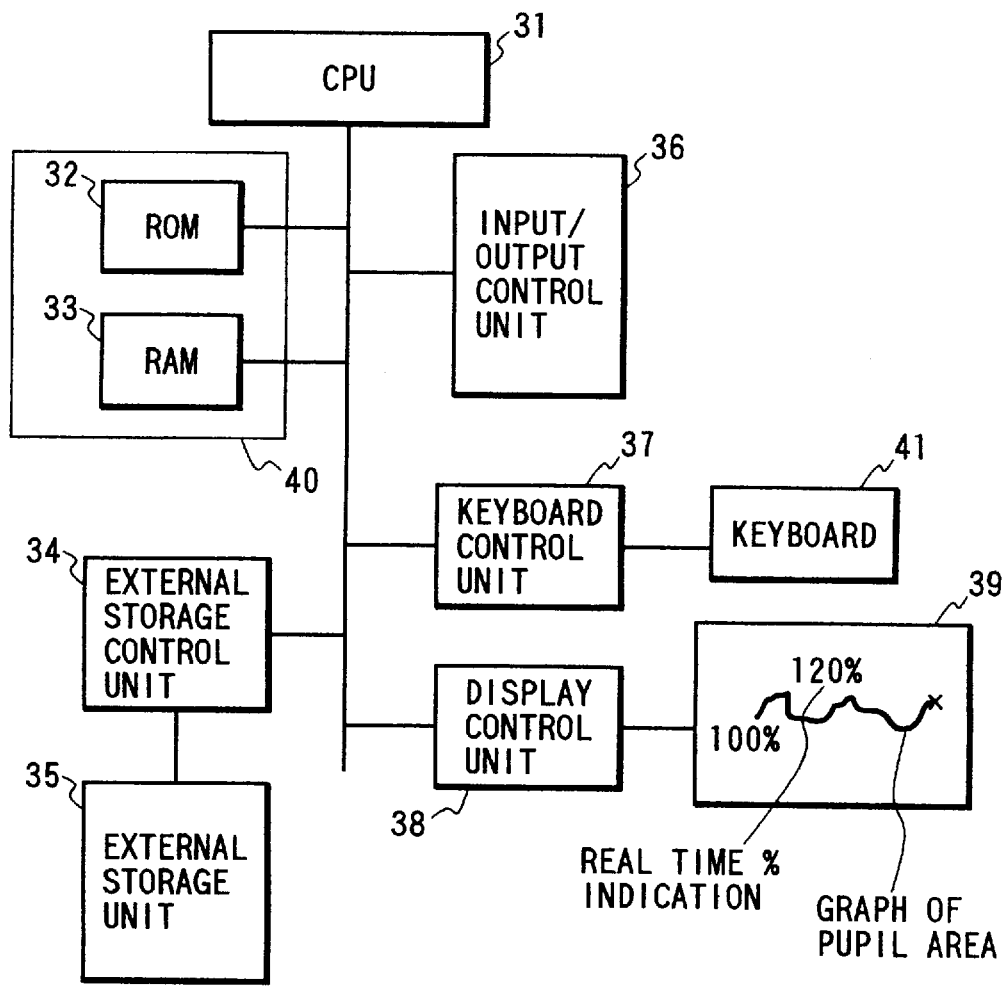
FIG. 4 is a diagram showing the configuration of a personal computer 25 shown in FIG. 3.

FIG. 4 shows the configuration of the personal computer 25. The personal computer 25 comprises: a CPU 31; a main memory 40 connected to the CPU 31; an external storage control unit 34; an input/output control unit 36; a keyboard control unit 37; a display control unit 38; and an external storage unit 35, a keyboard 41, and a display device 39 which are connected to the external storage control unit 34, the keyboard control unit 37, and the display control unit 38, respectively. The CPU 31 controls the whole of the personal computer 25, and performs controls of various parts and data processing on the basis of programs loaded into the main memory 40. The main memory 40 consists of a ROM 32 and a RAM 33. The ROM 32 stores programs and data which are required for the CPU 31 to execute programs read out from the external storage unit 35 to the RAM 33. Data required for the CPU 31 to perform data processing and results of the data processing are written into the RAM 33. The external storage unit 35 stores programs such as those shown in FIGS. 5 and 6.

Under instructions of the CPU 31, the external storage control unit 34 controls operations of reading data from and writing data into the external storage unit 35. The input/output control unit 36 controls the data transfer to external devices and transmission of control signals.

The keyboard 41 has plural keys. When one of the keys is pressed, the keyboard outputs a signal corresponding to the pressed key. Under instructions of the CPU 31, the keyboard control unit 37 controls the signal from the keyboard 41 and stores it into the RAM 33 of the main memory 40. The display device 39 visually displays given data on the screen. In the embodiment, a CRT is used of the CPU 31, the display control unit 38 controls the display device 39 so as to display data stored in the RAM 33 of the main memory 40.

A superimpose board 26 shown in FIG. 3 superimposes image data output from the area calculation board 23 over image data output from the personal computer 25. A video deck 27 records image data supplied from the superimpose board 26 and transmits the image data to a display device 28 which in turn displays the given data.

A motor driving unit 29 drives the motor 11 shown in FIG. 2 in accordance with the control signal output from the personal computer 25.

Figure 5:
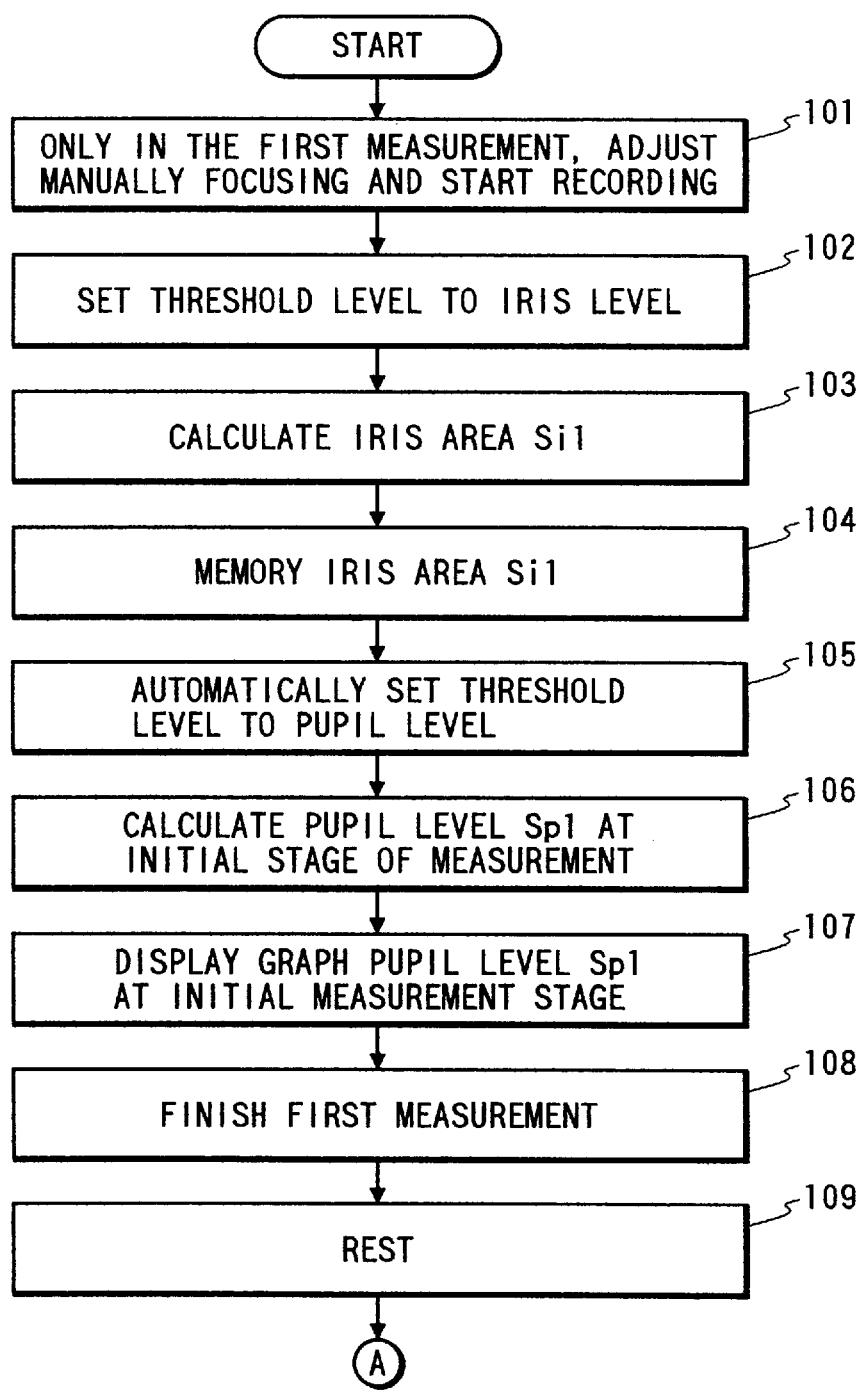
FIG. 5 is a flowchart illustrating the operation of the first embodiment.
Figure 6:
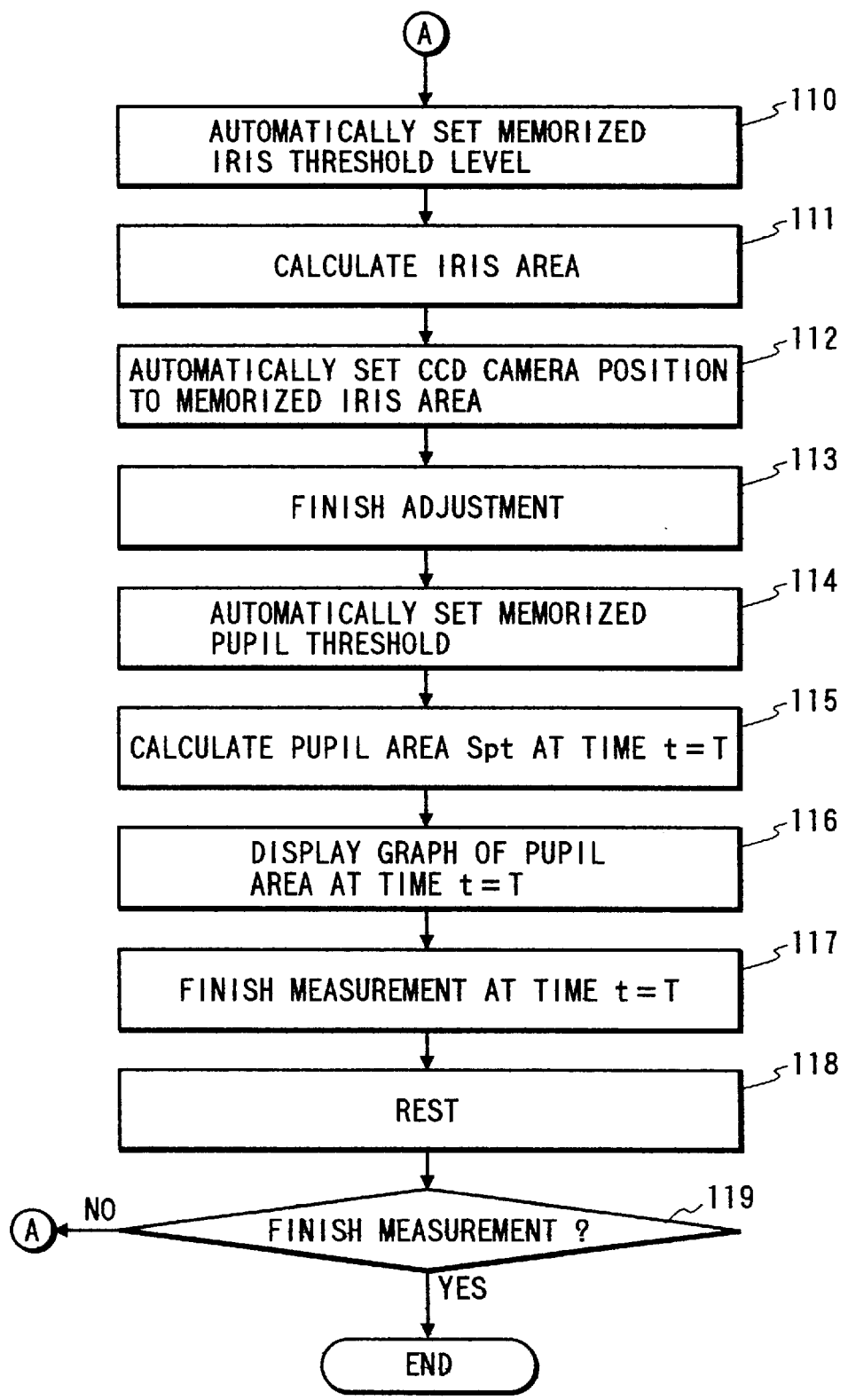
FIG. 6 is a flowchart illustrating the operation of the first embodiment.

In the embodiment, among processes performed by the CPU 31, step 104 shown in FIG. 5 corresponds to the iris data storing means, and step 112 shown in FIG. 6 to the controlling means.

Hereinafter, the operation of the thus configured pupil measuring apparatus will be described.

The apparatus is used for the diagnosis of Alzheimer's disease. The principle of the method in which the size of the pupil is measured to diagnose Alzheimer's disease is described in detail in U.S. Ser. No. 08/647,831.

Figure 7:
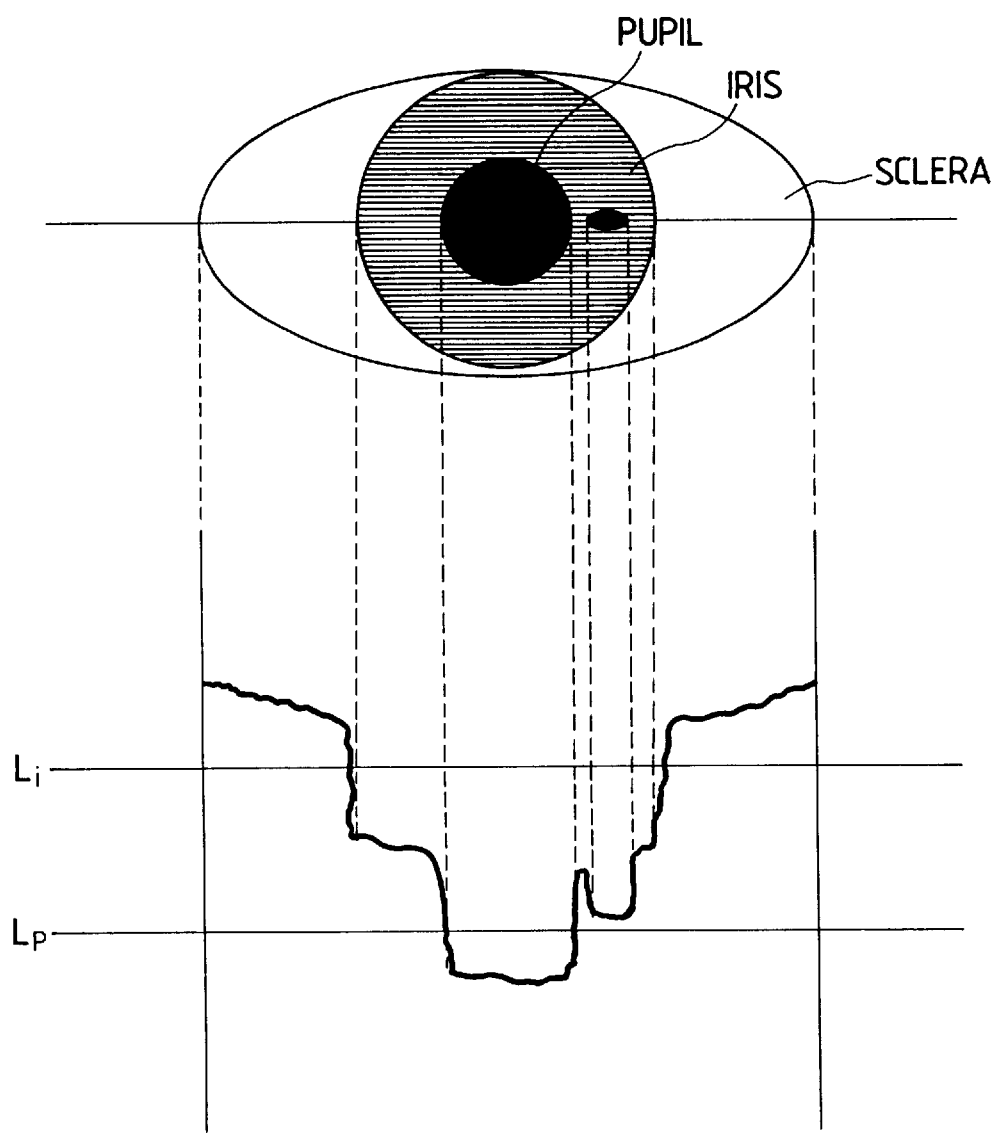
FIG. 7 is a diagram showing the brightness of an image of the front of the eyeball.

First, the operator operates the keyboard 41 so as to set the personal computer 25 to a pupil measurement mode. In response to this operation, the CPU 31 reads out the programs shown in the flowcharts of FIGS. 5 and 6 from the external storage unit 35 and then stores them into the RAM 33. Next, the operator drops one drop of a mydriasis diluent onto the left eye of the subject, and thereafter mounts the goggle 20 in which the shield plate 6 is removed from the right main unit 1b, on the subject. The operator then instructs the subject to see a mark positioned in the front by the right eye. Only in the first measurement, the operator manually adjusts the focusing and operates the keyboard 41 so as to instruct the CPU 31 to start the measurement. As a result, the CPU 31 instructs the CCU 22 to start the imaging process (step 101), turns on the LEDs 13, and controls the area calculation board 23 so as to set the threshold level to the iris level (step 102). Specifically, the level Li in the relationship between the image of the front of the eyeball and the brightness shown in FIG. 7 is set as the threshold level.

Next, the CPU 31 outputs instructions of the start of the area calculation to the area calculation board 23 (step 103). In response to the instructions, the area calculation board 23 extracts a part of the image of one screen at the present time, the brightness of the part being not higher than the level Li, from the image data output from the imaging apparatus 21, and calculates the area Si1 of the part. The digital value of the calculation result is supplied to the personal computer 25. The CPU 31 of the personal computer 25 stores the area value into the RAM 33 (step 104). That is, the area value of the iris which will be used as the reference is stored.

The CPU 31 controls the area calculation board 23 so as to set the threshold level which is to be used in the calculation, to the level of the pupil (step 105). Specifically, the level Lp in the front of the eyeball and the brightness shown in FIG. 7 is set as the threshold level.

The CPU 31 then outputs instructions of the start of the area calculation to the area calculation board 23 (step 106). In response to the instructions, the area calculation board 23 extracts a part of the image of one screen at the present time, the brightness of the part being not higher than the level Lp, from the image data output from the imaging apparatus 21. The area calculation board supplies the image of the part to the superimpose board 26 and calculates the area Sp1 of the part. The digital value of the calculation result is supplied to the personal computer 25. The personal computer 25 converts the area value into data for a graph display, outputs the data to the superimpose board 26, and stores the data into the RAM 33 (step 107). The superimpose board 26 superimposes the image data for a graph display output from the personal computer 25 over the image data of the pupil output from the area calculation board 23, and transmits the resulting superimposed image data to the video deck 27. The video deck 27 records the superimposed image data and transmits them to the display device 28. The display device 28 displays the given data.

When the first measurement is completed, the CPU 31 sets the next measurement time t=T in a measurement time area of the RAM 33, and controls the display device 39 of the personal computer 25 so as to display the time. When the measurements are to be conducted at intervals of seven minutes, for example, seven minutes are added to the starting time of the first measurement. The resulting time is set in the measurement time area and displayed on the display device 39.

When the time is displayed, the operator dismounts the goggle 20 from the subject, and frees the subject from the measurement until the time of the next measurement arrives. When the time of the next measurement approaches, the operator mounts the goggle 20 on the subject (step 109). When the time comes, the CPU 31 controls the area calculation board 23 so as to set the threshold level which is to be used in the calculation, to the level Li of the iris (step 110).

The CPU 31 then outputs instructions of the start of the area calculation to the area calculation board 23 (step 111). In response to the instructions, the area calculation board 23 extracts a part of the image of one screen at the present time, the brightness of the part being not higher than the level Li, from the image data output from the imaging apparatus 21. The area calculation board calculates the area of the part and supplies the digital value of the calculation result to the personal computer 25. The CPU 31 controls the motor driving unit 29 so that the area value supplied from the area calculation board 23 coincides with the area which is stored in the first measurement and used as the reference of the iris. In other words, the CPU 31 automatically adjusts the position of the CCD camera 7. When the area of the reference is larger, for example, the CPU 31 causes the motor 11 to rotate so that the CCD camera 7 approaches the eye, and, when the area of the reference is smaller, the CPU 31 causes the motor 11 to rotate so that the CCD camera 7 separates from the eye. When the CPU 31 ascertains that the areas coincide with each other, the CPU terminates the control (step 113).

The CPU 31 then controls the area calculation board 23 so as to set the threshold level which is to be used in the calculation, to the level Lp of the pupil (step 114).

Next, the CPU 31 outputs instructions of the start of the area calculation to the area calculation board 23 (step 115). In response to the instructions, the area calculation board 23 extracts a part of the image of one screen at the present time, the brightness of the part being not higher than the level Lp, from the image data output from the imaging apparatus 21. The area calculation board supplies the image of the parates the area of the part. The digital value of the calculation result is supplied to the personal computer 25. The CPU 31 of the personal computer 25 obtains display data from the area value, outputs the data to the superimpose board 26, and stores the data into the RAM 33 (step 116). The display data include data for a graph which shows relationships between the measurement time and the area value, and the percentage of the pupil area obtained in the present measurement to that obtained in the first measurement. The superimpose board 26 superimposes the data for a graph display supplied from the personal computer 25 over the image data of the pupil supplied from the area calculation board 23, and transmits the superimposed image data to the video deck 27. The video deck 27 records the superimposed image data and transmits them to the display device 28. The display device 28 displays the given data.

When the present measurement is completed, the CPU 31 sets the next measurement time t=T in the measurement time area of the RAM 33, and controls the display device 39 of the personal computer 25 so as to display the time (step 117). When the measurements are to be conducted at intervals of seven minutes, for example, seven minutes are added to the starting time of the present measurement. The resulting time is set in the measurement time area and displayed on the display device 39.

The CPU 31 waits until the time of the next measurement comes (step 118). When the time comes, the CPU 31 judges whether the measurement is to be terminated or not (step 119). If the measurement is not to be terminated, the CPU 31 returns to step 110, and, if the measurement is to be terminated, the measurement is terminated. This judgement is performed based on whether the preset time reaches a time which is previously stored or not, or whether instructions of termination are input through the keyboard 41 or not.

When the above-described processing is performed, as shown in FIG. 3, a graph showing relationships between the measurement time and the area value, the percentage of the pupil area obtained in the present measurement to that obtained in the first measurement, and the image of the pupil obtained in the present measurement are displayed in a superimposed manner on the screen of the display device 28.

According to the goggle 20 used in the embodiment, the CCD camera 7 can be moved by a simple configuration.

According to the pupil measuring apparatus of the embodiment, when instructions of the start of the measurement are once given, each measurement is automatically started when a preset time comes. Therefore, the apparatus can be very easily operated.

Second embodiment

Figure 8:
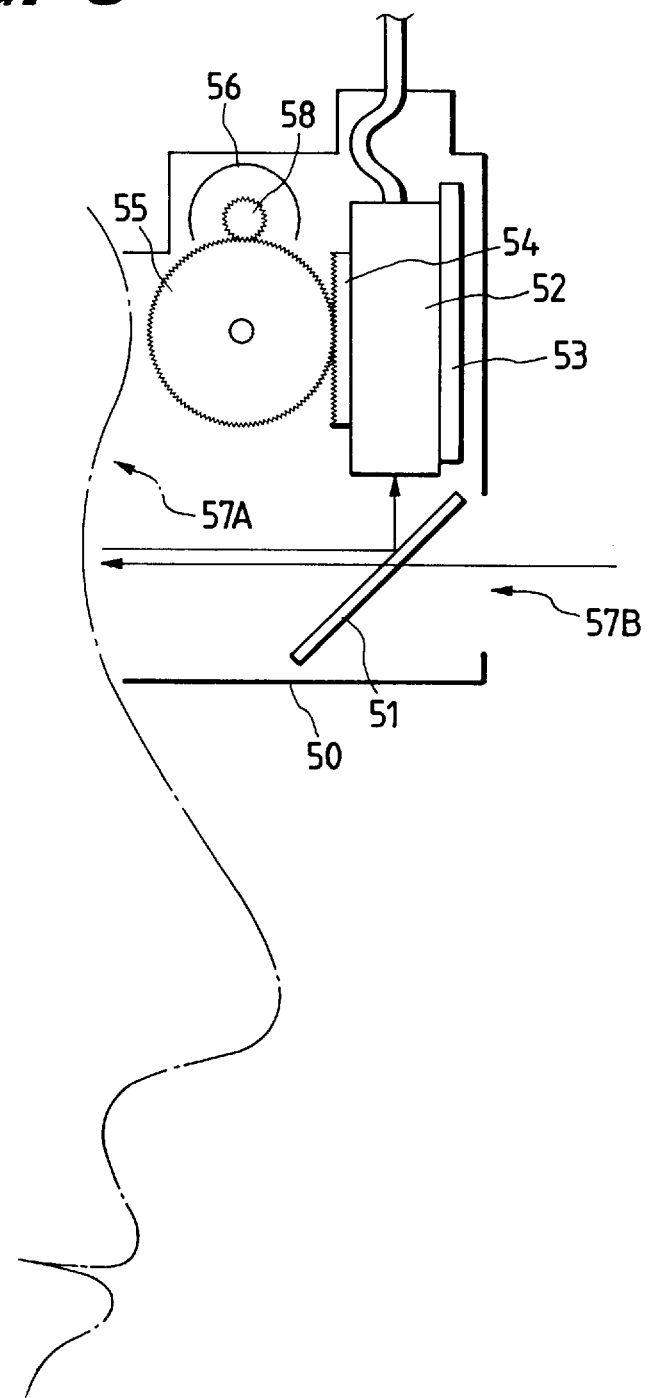
FIG. 8 is a view showing the internal configuration of a goggle which is used in a second embodiment.

Next, a second embodiment will be described. The embodiment is different from the first embodiment only in the structure of the left main unit of the pupil measuring goggle. As shown in FIG. 8, a left main unit 50 of the embodiment has a half mirror 51 which reflects light from an inner opening 57A and which allows light from an outer opening 57B to be transmitted therethrough so as to reach the inner opening 57A. A fixed focus CCD camera 52 which is disposed so as to receive light reflected from the half mirror 51 is supported by a guide rail 53 in such a manner that the camera is reciprocally movable with respect to the half mirror 51 in the direction of the reflected light. A rack 54 is attached onto the outer face of the CCD camera 52 so as to elongate in the longitudinal direction of the camera. A gear 55 which meshes with the rack 54 is attached to the left main unit 50. Furthermore, a motor 56 is attached to the left main unit 50. A gear 58 attached to the rotation shaft of the motor 56 meshes with the gear 55. The other portions of the pupil measuring apparatus of the embodiment are configured in the same manner as those of the first embodiment.

In the embodiment, the goggle is configured as described. When the right main unit 1b of the goggle is included and the goggle of this state are mounted on the subject, therefore, the subject can easily stare at a mark positioned outside the goggle by the both eyes. At this time, the center of the pupil reaches the optical axis of the CCD camera 52, and the pupil remains at this position, with the result that correct images of the pupil and the iris can be obtained.

Third embodiment

Figure 9:
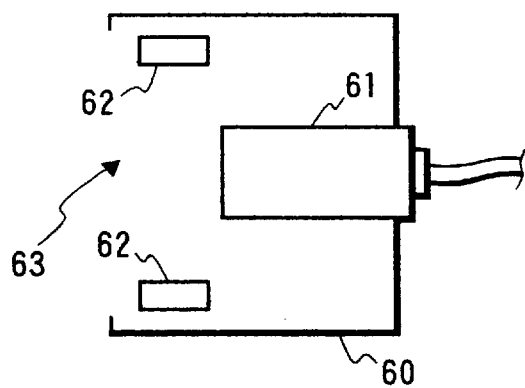
FIG. 9 is a view showing the internal configuration of a goggle which is used in a third embodiment.

Next, a third embodiment will be described. A pupil measuring goggle of the embodiment is different from that of the above-described first embodiment in the following point. As shown in FIG. 9, in a left main unit 60 of the embodiment, a fixed focus CCD camera 61 is disposed at the front so as to receive light through an-opening 63. A plurality of LEDs 62 which emit infrared light are disposed in the left main unit 60 so as to be directed toward the opening 63. In other words, in the goggle, the CCD camera 61 is merely fixed to the left main unit 60 and not provided with moving means.

Figure 10:
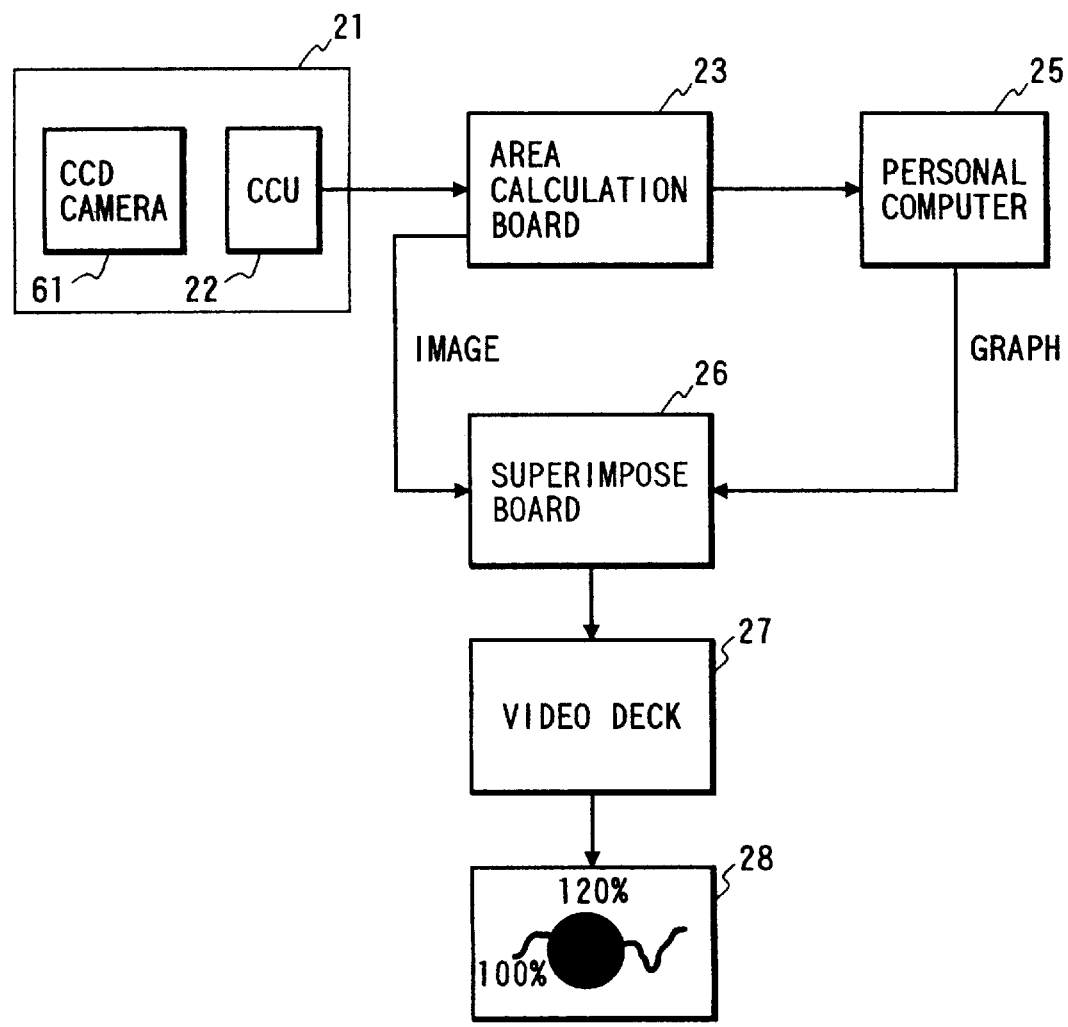
FIG. 10 is a block diagram showing the whole configuration of the third embodiment.

FIG. 10 shows the whole configuration of a pupil measuring apparatus in which the goggle is used. The apparatus is identical with the first embodiment shown in FIG. 3 except that the motor driving unit 29 and the motor 12 are omitted. In the embodiment, however, the external storage unit 35 of the personal computer 25 stores the programs such as those shown in the flowchart of FIG. 11. In the embodiment, among processes performed by the CPU 31, step 214 shown in FIG. 11 corresponds to the correcting means.

Hereinafter, the operation of the pupil measuring apparatus will be described. The apparatus also is used for the diagnosis of Alzheimer's disease, and the goggle can be frequently mounted on and dismounted from the subject.

The operator operates the keyboard 41 so as to set the personal computer 25 to a pupil measurement mode. In response to this operation, the CPU 31 reads out the programs shown in the flowchart of FIG. 11 from the external storage unit 35 and then stores them into the RAM 33. Next, the operator drops one drop of a mydriasis diluent onto the left eye of the subject, and thereafter mounts the goggle on the subject. The operator then operates the keyboard 41 so as to instruct the CPU 31 to start the measurement.

Figure 11:
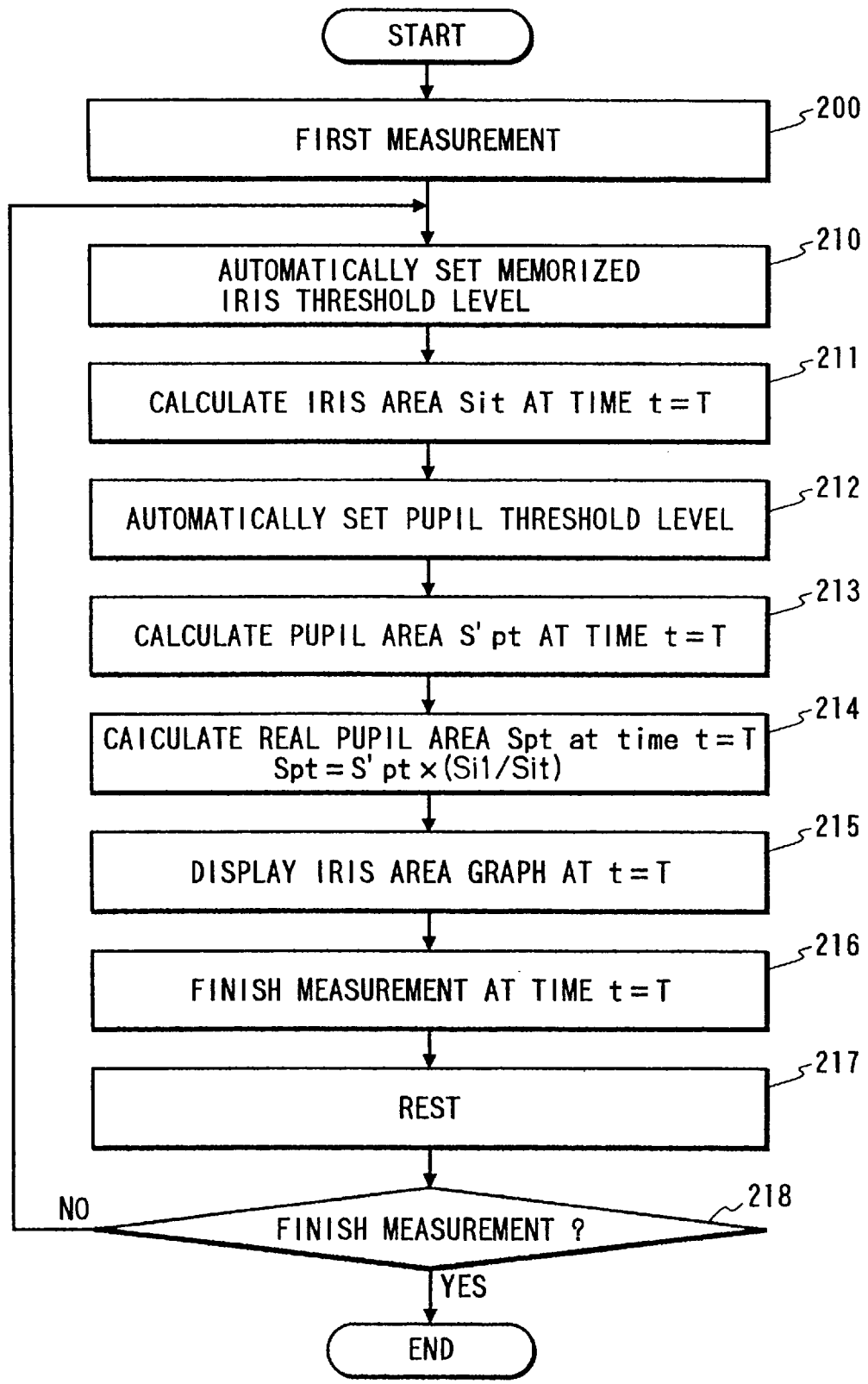
FIG. 11 is a flowchart illustrating the operation of the third embodiment.

Among processes which are thereafter performed by the CPU 31, step 200 shown in FIG. 11 or the process of a first measurement is identical with that of steps 101 to 105 of FIG. 5 which have been described in the first embodiment, and hence detailed description of the area calculation board 23 so as to set the threshold level which is to be used in the calculation, to the level Li of the iris (step 210).

The CPU 31 then outputs instructions of the start of the area calculation to the area calculation board 23 (step 211). In response to the instructions, the area calculation board 23 extracts a part of the image of one screen at the present time, the brightness of the part being not higher than the level Li, from the image data output from the imaging apparatus 21. The area calculation board calculates the area Sit of the part and supplies the digital value of the calculation result to the personal computer 25. The CPU 31 stores the area value supplied from the area calculation board 23 into the RAM 33.

The CPU 31 controls the area calculation board 23 so as to set the threshold level which is to be used in the calculation, to the level Lp of the pupil (step 212).

The CPU 31 outputs instructions of the start of the area calculation to the area calculation board 23 (step 213). In response to the instructions, the area calculation board 23 extracts a part of the image of one screen at the present time, the brightness of the part being not higher than the level Lp, from the image data output from the imaging apparatus 21. The area calculation board supplies the image of the part to the superimpose board 26 and calculates the area S'pt of the part. The digital value of the calculation result is supplied to the personal computer 25. The CPU 31 of the personal computer 25 stores the area value into the RAM 33.

The CPU 31 calculates the real pupil area Spt at the present measurement time t=T (step 214), or calculates Spt=S'pt×(Si1/Sit) where Si1 indicates the value of the iris area obtained in the first measurement. The CPU 31 then obtains display data from the obtained real pupil area Spt, outputs the data to the superimpose board 26, and stores the data into the RAM 33 (step 215). The display data include data for measurement time and the area value, and the percentage of the pupil area obtained in the present measurement to that obtained in the first measurement. The superimpose board 26 superimposes the data for a graph display supplied from the personal computer 25 over the image data of the pupil supplied from the area calculation board 23, and transmits the superimposed image data to the video deck 27. The video deck 27 records the superimposed image data and transmits them to the display device 28. The display device 28 displays the given data.

When the present measurement is completed, the CPU 31 sets the next measurement time t=T in the measurement time area of the RAM 33, and controls the display device 39 of the personal computer 25 so as to display the time (step 216). When the measurements are to be conducted at intervals of seven minutes, for example, seven minutes are added to the starting time of the present measurement. The resulting time is set in the measurement time area and displayed on the display device 39.

The CPU 31 waits until the time of the next measurement comes (step 217). When the time comes, the CPU 31 judges whether the measurement is to be terminated or not (step 218). If the measurement is not to be terminated, the CPU 31 returns to step 210, and, if the measurement is to be terminated, the measurement is terminated. This judgement is performed based on whether the preset time reaches a time which is previously stored or not, or whether instructions of termination are input through the keyboard 41 or not.

When the above-described processing is performed, as shown in FIG. 10, a graph showing relationships between the measurement time and the area value, the percentage of the pupil area obtained in the present measurement to that obtained in the first measurement, and the image of the pupil obtained in the present measurement are displayed in a superimposed manner on the screen of the display device 28. In other words, corrected data of the pupil area are displayed each time a measurement is conducted.

According to the embodiment, the goggle has a simple configuration and hence can be very easily produced.

Fourth embodiment

Figure 12:
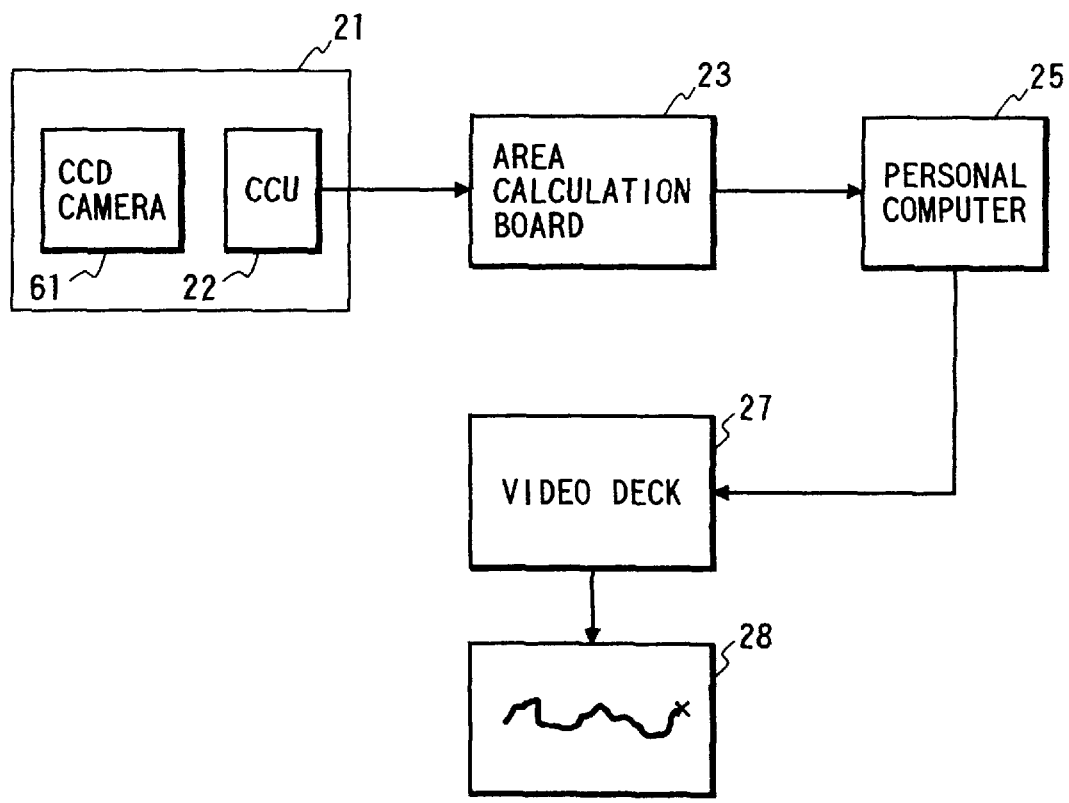
FIG. 12 is a block diagram showing the whole configuration of a fourth embodiment.

Next, a fourth embodiment will be described. A pupil measuring goggle of the embodiment is configured in the same manner as that of the third embodiment. FIG. 12 shows the whole configuration of a pupil measuring apparatus in which the goggle is used. Specifically, the apparatus has a configuration which is identical with that shown in FIG. 10 except that the superimpose board 26 is omitted. The image data output from the personal computer 25 are directly supplied to the video deck 27. In the apparatus, the external storage unit 35 of the personal computer 25 shown in FIG. 4 stores the programs such as those shown in the flowchart of FIG. 13.

Hereinafter, the operation of the pupil measuring apparatus will be described. The apparatus also is used for the diagnosis of Alzheimer's disease, and the goggle can be frequently mounted on and dismounted from the subject.

Among the works to be conducted by the operator and the processes to be performed by the CPU 31 in accordance with the works, step 300 shown in FIG. 13 or the process of a first measurement is identical with that of steps 101 to 109 of FIG. 5 which have been described in the first embodiment, and hence detailed description of the process is omitted.

The CPU 31 controls the area calculation board 23 so as to set the threshold level which is to be used in the calculation, to the level Li of the iris (stept of the area calculation to the area calculation board 23 (step 311). In response to the instructions, the area calculation board 23 extracts a part of the image of one screen at the present time, the brightness of the part being not higher than the level Li, from the image data output from the imaging apparatus 21. The area calculation board calculates the area of the part and supplies the digital value of the calculation result to the personal computer 25. The CPU 31 stores the area value supplied from the area calculation board 23 into the RAM 33.

The CPU 31 controls the area calculation board 23 so as to set the threshold level which is to be used in the calculation, to the level Lp of the pupil (step 312). The CPU 31 outputs instructions of the start of the area calculation to the area calculation board 23 (step 313). In response to the instructions, the area calculation board 23 extracts a part of the image of one screen at the present time, the brightness of the part being not higher than the level Lp, from the image data output from the imaging apparatus 21. The area calculation board supplies the image of the part to the superimpose board 26 and calculates the area Srpt of the part. The digital value of the calculation result is supplied to the personal computer 25. The personal computer 25 stores the area value into the RAM 33.

When the present measurement is completed, the CPU 31 sets the next measurement time t=T in the measurement time area of the RAM 33, and controls the display device 39 of the personal computer 25 so as to display the time (step 314). When the measurements are to be conducted at intervals of seven minutes, for example, seven minutes are added to the starting time of the present measurement. The resulting time is set in the measurement time area and displayed on the display device 39.

The CPU 31 waits until the time of the next measurement comes (step 315). When the time comes, the CPU 31 judges whether the measurement is to measurement is not to be terminated, the CPU 31 returns to step 310, and, if the measurement is to be terminated, the measurement is terminated. This judgement is performed based on whether the preset time reaches a time which is previously stored or not, or whether instructions of termination are input through the keyboard 41 or not.

If the CPU 31 judges in step 316 that the measurement is to be terminated, the CPU 31 calculates the real pupil area Spt at the measurement time t=T from the data stored in the RAM 33 (step 214), or calculates Spt=S'pt×(Sil/Sit) where Sil indicates the value of the iris area obtained in the first measurement. The CPU 31 then judges whether the real pupil area has been obtained for all the measurement times or not (step 318). If No, the CPU 31 returns to step 317. If all the real pupil areas have been obtained, the real pupil areas for all the measurement times are displayed in the form of a graph (step 319).

When the above-described process is performed, a graph which shows relationships-between the measurement time and the area value is displayed on the display device 28 after all the measurements are conducted.

In the same manner as the third embodiment, according to the embodiment, the goggle has a simple configuration and hence can be very easily produced.

In all the embodiments described above, the goggle and the whole apparatus are configured so as to observe only one of the eyes. Alternatively, they may be configured so as to observe both eyes. For example, a movable CCD camera may be disposed in each of the right and left main units of the goggle and video signals of the CCD cameras are processed so that the sizes of the pupils of both eyes are measured. When Alzheimer's disease is to be diagnosed by using such an apparatus which can measure both eyes, for example, the sizes of the pupils of the eyes are measured after a mydriasis diluent is dropped onto one of the eyes and physiological saline is dropped onto the other eye. In this case, when the variation of the pupil area of the eye onto which the mydriasis diluent is dropped is to be observed, it is possible to reference that of the pupil area of the other eye onto which physiological saline is dropped, thereby enabling the measurement to be more correctly conducted. In all the embodiments described above, the areas of the pupil and iris are obtained. Alternatively, the diameters of the pupil and iris may be obtained. Also in the alternative, the same effects can be attained.

According to the present invention, the distance between the eyeball surface and the video camera can be easily changed without changing the mounting state of the goggle.

The present invention can attain the effect that the subject wearing the goggle can easily stare at a mark positioned outside the goggle by both eyes and hence the measurement resulting in that the measurement is conducted very correctly.

According to the present invention, it is not necessary to perform an operation of eliminating an error which is due to the mounting state of the goggle each time the goggle is mounted. Furthermore, correct measurement results can be obtained.

According to the present invention can be attained by using the goggle of a simple configuration.

What is claimed is:

1. An eyeball surface measuring apparatus comprising:

a main unit to be mounted on a face of a subject;

a video camera;

video camera holding means, disposed in said main unit, for holding said video camera, when said main unit is mounted on said face of said subject, such that said video camera is directed to an eyeball of said subject and said video camera is movable along an optical axis of said video camera;

moving means for moving said video camera, which is held by said video camera holding means, along said optical axis;

iris data storing means for storing data indicative of a size of an iris used as reference; and controlling means for controlling said moving means in order to cause a measured size of an iris of said eyeball obtained on the basis of an output of said video camera to coincide with said size of an iris stored in said iris data storing means.

2. An eyeball surface measuring apparatus comprising:

a main unit to be mounted on a face of a subject;

a video camera;

video camera holding means, disposed in said main unit, for holding said video camera, when said main unit is mounted on said face of said subject, such that said video camera is directed to an eyeball of said subject and said video camera is movable along an optical axis of said video camera;

moving means for moving said video camera, which is held by said video camera holding means, along said optical axis;

a half mirror disposed in said main unit, wherein said video camera holding means holds said video camera in a state where said video camera is directed to said eyeball in a direction along which an image of said eyeball is reflected from said half mirror;

iris data storing means for storing data indicative of a size of an iris used as a reference; and controlling means for controlling said moving means in order to cause a measured size of an iris of said eyeball obtained on the basis of an output of said video camera to coincide with said size of an iris stored in said iris data storing means.

3. An eyeball surface measuring apparatus comprising:

a main unit to be mounted on a face of a subject;

a video camera;

video camera holding means, disposed in said main unit, for holding said video camera, when said main unit is mounted on said face of said subject, such that said video camera is directed to an eyeball of said subject and said video camera is movable along an optical axis of said video camera;

moving means for moving said video camera, which is held by said video camera holding means, along said optical axis;

iris data storing means for storing data indicative of a size of an iris used as a reference; and correcting means for correcting a measured size of a pupil of said eyeball which is obtained on the basis of an output of said video camera by referencing a measured size of an iris of said eyeball which is obtained from said output of said video camera and on the basis of said data, stored in said iris data storing means, indicative of a size of an iris, wherein said data indicative of a size of an iris has been obtained in a mounting state in which said main unit is mounted on said face of said subject.

4. An eyeball surface measuring apparatus comprising:

a main unit to be mounted on a face of a subject;

a video camera;

video camera holding means, disposed in said main unit, for holding said video camera, when said main unit is mounted on said face of said subject, such that said video camera is directed to an eyeball of said subject and said video camera is movable along an optical axis of said video camera;

moving means for moving said video camera, which is held by said video camera holding means, along said optical axis;

a half mirror disposed in said main unit, wherein said video camera holding means holds said video camera in a state where said video camera is directed to said eyeball in a direction along which an image of said eyeball is reflected from said half mirror;

iris data storing means for storing data indicative of a size of an iris used as a reference; and correcting means for correcting a measured size of a pupil of said eyeball which is obtained on the basis of an output of said video camera by referencing a measured size of an iris of said eyeball which is obtained from said output of said video camera and on the basis of said data, stored in said iris data storing means, indicative of a size of an iris, wherein said data indicative of a size of an iris has been obtained in a mounting state in which said main unit is mounted on said face of said subject.

5. An eyeball surface measuring apparatus comprising:

a main unit to be mounted on a face of a subject;

a video camera;

video camera holding means, disposed in said main unit, for holding said video camera, when said main unit is mounted on said face of said subject, such that said video camera is directed to an eyeball of said subject; and iris data storing means for storing data indicative of a size of an iris used as a reference; and correcting means for correcting a measured size of a pupil of said eyeball which is obtained on the basis of an output of said video camera be referencing a measured size of an iris of said eyeball which is obtained from said output of said video camera and on the basis of said data, stored in said iris data storing means, indicative of a size of an iris, wherein said data indicative of a size of an iris has been obtained in a mounting state in which said main unit is mounted on said face of said subject.

* * * * *